(12) United States Patent
Merz

(10) Patent No.: US 12,011,339 B2
(45) Date of Patent: Jun. 18, 2024

(54) EARS DISIMPACTOR

(71) Applicant: Guy Francis Merz, Glendale, AZ (US)

(72) Inventor: Guy Francis Merz, Glendale, AZ (US)

( * ) Notice: Subject to any disclaimer, the term of this patent is extended or adjusted under 35 U.S.C. 154(b) by 906 days.

(21) Appl. No.: 17/001,709

(22) Filed: Aug. 25, 2020

(65) Prior Publication Data
US 2022/0062054 A1 Mar. 3, 2022

(51) Int. Cl.
*A61F 11/00* (2022.01)
*A61M 1/00* (2006.01)
*A61M 3/02* (2006.01)

(52) U.S. Cl.
CPC ............ *A61F 11/006* (2013.01); *A61M 1/92* (2021.05); *A61M 3/0266* (2013.01); *A61M 3/0283* (2013.01); *A61M 3/0202* (2021.05); *A61M 2205/36* (2013.01); *A61M 2206/12* (2013.01); *A61M 2210/0662* (2013.01)

(58) Field of Classification Search
CPC ............ A61F 11/006; A61F 11/00–30; A61M 2210/0662–0675; A61M 1/92; A61M 3/0266; A61M 3/0283; A61M 3/0202; A61M 3/02; A61M 2205/36; A61M 2206/12; A61M 1/71; A61B 2018/00327; A61B 1/227; A61B 17/24; A61B 2017/00685
See application file for complete search history.

(56) References Cited

U.S. PATENT DOCUMENTS

| 6,187,021 | B1 | 2/2001 | Wim |
| 6,485,451 | B1 | 11/2002 | Roberts et al. |
| 6,554,799 | B1* | 4/2003 | Hatamura ............... A61F 11/20 29/889 |
| 8,062,216 | B2 | 11/2011 | Raghuprasad |
| 8,876,707 | B2 | 11/2014 | Wellen et al. |
| 10,154,927 | B2 | 12/2018 | Fahn et al. |
| 10,238,545 | B2 | 3/2019 | Kraitzer et al. |
| 2006/0206134 | A1* | 9/2006 | Conquergood ............ A61B 17/320016 606/180 |
| 2010/0137814 | A1* | 6/2010 | Chew ................. A61M 3/0279 604/257 |

(Continued)

FOREIGN PATENT DOCUMENTS

| BR | 102016019440 B1 | 7/2019 |
| CN | 105266958 A | 1/2016 |

*Primary Examiner* — Darwin P Erezo
*Assistant Examiner* — Brigid K Byrd
(74) *Attorney, Agent, or Firm* — Ashok Tankha

(57) ABSTRACT

An ear disimpactor for disimpacting material impacted in an ear canal and against a tympanic membrane, is disclosed. The impacted material comprises cerumen, insects, and other debris. The ear disimpactor comprises a housing, a warm water irrigation unit, and a suction unit. The housing comprises an ear speculum attached to an outer surface of the housing, a motorized auger comprising a drill bit extending from the motorized auger to a tip of the ear speculum, a warm water line extending from the tip of the ear speculum and across a length of the housing, and a suspension suction tube extending from the tip of the speculum and across the length of the housing. The warm water irrigation unit provides warm water to the ear canal through the warm water line and the suction unit sucks out suspension from the ear canal.

10 Claims, 11 Drawing Sheets

(56) References Cited

U.S. PATENT DOCUMENTS

| | | |
|---|---|---|
| 2011/0015489 A1* | 1/2011 | Raghuprasad ......... A61B 1/227 |
| | | 600/187 |
| 2013/0023914 A1 | 1/2013 | Truong et al. |
| 2015/0374964 A1* | 12/2015 | Verhoeven .......... A61M 5/1428 |
| | | 604/247 |
| 2016/0135995 A1 | 5/2016 | Burres |
| 2018/0000499 A1* | 1/2018 | Altman ............ A61B 17/32002 |
| 2019/0143029 A1* | 5/2019 | Diwan ................ A61M 3/0275 |
| | | 606/162 |
| 2020/0060643 A1* | 2/2020 | Misener ............... A61B 5/0035 |
| 2020/0214894 A1* | 7/2020 | Kim .................... A61M 3/0258 |

* cited by examiner

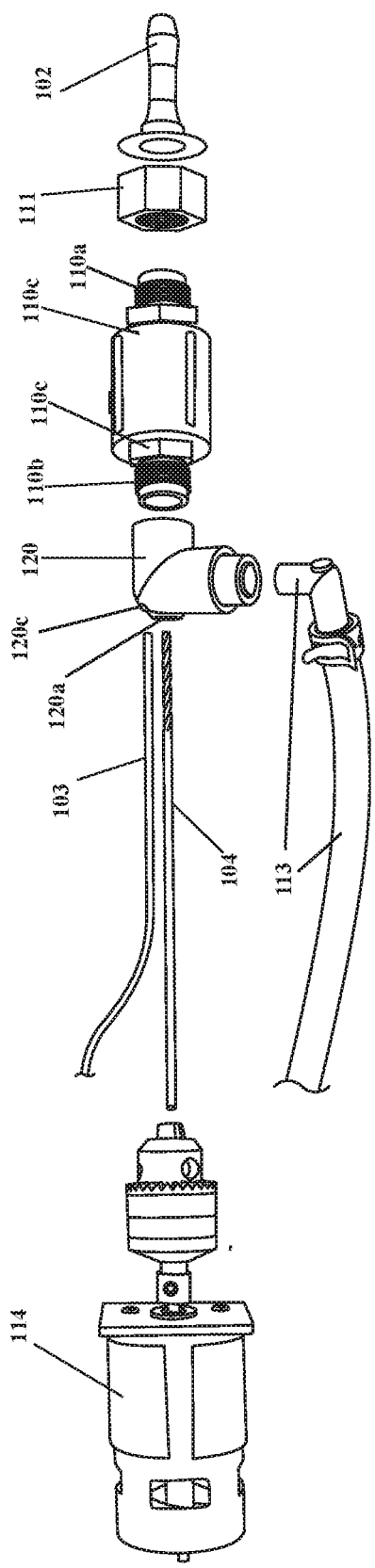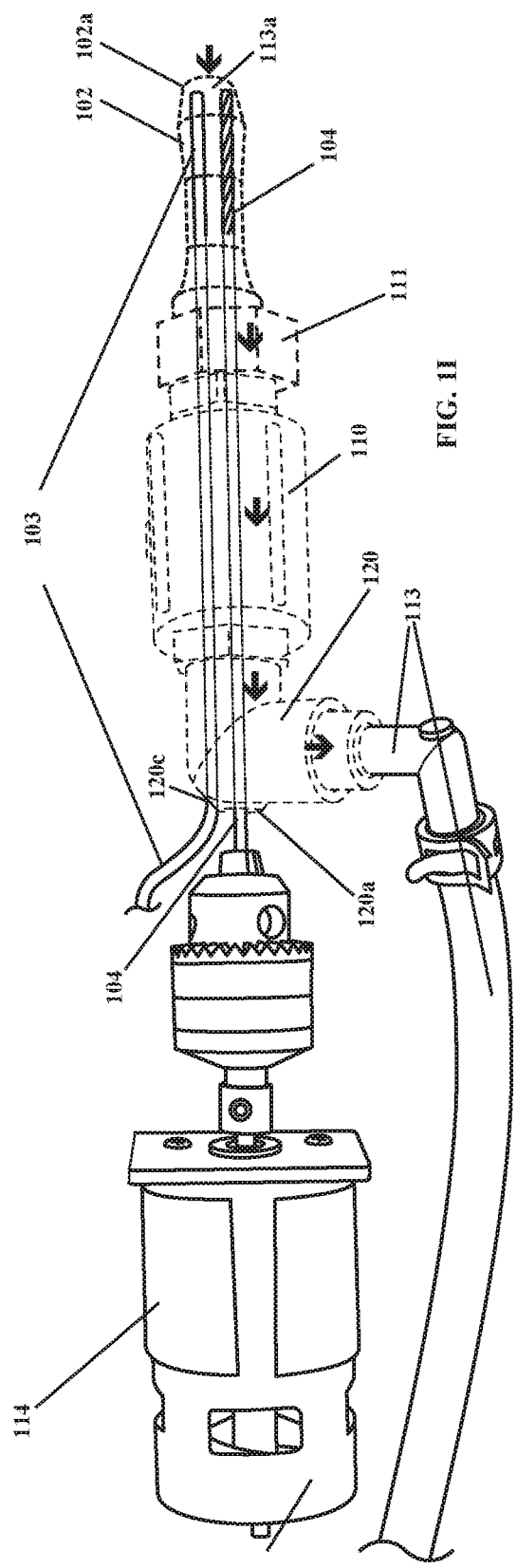
FIG. 1H
FIG. 1I

EARS DISIMPACTOR

FIELD OF THE INVENTION

The present invention relates to an apparatus for disimpacting cerumen, insects and other debris, from an ear canal. More specifically, the present invention relates to an ear disimpactor for disimpacting material impacted in the ear canal and against a tympanic membrane comprising cerumen, insects, and other debris, hereafter referred to as impacted material, using warm water irrigation, a rotating drill bit to grind the impacted material into a impacted material-water suspension, hereafter referred to as a suspension, by creating a cyclonic action inside the ear canal to loosen and allow removal of the impacted material from the ear canal by a suction unit, and to thereafter discharge the suspension into a debris container.

BACKGROUND

Disimpacting impacted material from an ear canal is a painful procedure for the patient and time consuming for both the patient and physician. A common technique used to disimpact impacted material from the ear canal of a patient is to squirt water into the ear canal with a plastic cannula and a syringe to try and get the water behind the cerumen and drain the impacted material out of the ear canal with a stream of water. This procedure is uncomfortable for the patient and often unsuccessful, necessitating use of an ear curettage. An ear curette is used to manually tease impacted material out of the ear canal, often causing pain, abrasions and bleeding of a wall of the ear canal. The patient is often sent home with a prescription for an ear wax softener and requested to make a return visit for another attempt to disimpact the impacted material from the ear canal.

US patent application No. 20130023914A1 discloses an exemplary device that uses a curette with irrigation for removing ear wax. The tool 401, as shown in FIGS. 27-28 of the USPTO patent application No. 20130023914A1, includes a housing 403 and an elongated body 405. A proximal end of the body includes a handle portion 407. A portion of the body 405 defines a lumen therethrough. In the exemplary tool, the lumen extends from a distal most tip to the housing 403. The lumen is configured as a suction channel. Irrigation is provided through an inlet 409. The tool includes a curette instrument. The curette is similar to a conventional curette with a working end for removing ear wax. Other instruments may be provided including, but not limited to, forceps, a grasper, a cutting tool, a drug delivery tool, ablation device, and more. The curette is elongated and extends within the lumen. Suction and/or irrigation are provided around the curette body. In various embodiments, the instrument is configured to collapse and expand. The exemplary tool has three operational modes: tool, tool and suction, and suction. In the tool mode, a user can operate the curette tool. In the combined tool and suction mode, the tool is used while suction is available. This may be useful for performing biopsies, removing stenoses, clearing a path in impacted ear wax, and the like. In the suction mode, the tool can operate similar to a conventional suction device. In this method, a technician tries to manually tease the ear wax out, often causing pain, abrasions and bleeding of the wall of the ear canal. The patient is often sent home with a prescription for an ear wax softener and required to make a return visit for another attempt to disimpact the impacted material.

Therefore, there is a long felt need for an apparatus that disimpacts impacted material from an ear canal. There is also a long felt need for an apparatus that alleviates the painful procedure for disimpacting impacted material from the ear canal of a patient.

SUMMARY OF THE INVENTION

This summary is provided to introduce a selection of concepts in a simplified form that are further disclosed in the detailed description of the invention. This summary is not intended to determine the scope of the claimed subject matter.

The ear disimpactor disclosed herein addresses the above recited need for an apparatus that disimpacts impacted material from an ear canal and material impacted against the tympanic membrane. The ear disimpactor disclosed herein also addresses the above recited need for an apparatus that alleviates the painful procedure of removal of impacted material from a patient's ear canal and against the tympanic membrane (ear drum) using warm water irrigation, a rotating auger and suction.

The ear disimpactor comprises a housing, a warm water irrigation unit, and a suction unit. The housing comprises an ear speculum attached to an outer surface of the housing, a motorized auger comprising a drill bit, a warm water line extending across a length of the housing to the ear speculum, and a suspension suction tube extending from the end of the speculum and across the length of the housing. The drill bit extends from the motorized auger to the ear speculum. The warm water line extends through the housing and an outlet screwed fitting through which the warm water line and the drill bit of the motorized auger are configured to engage with the outer ear. The suspension suction tube extends through the housing to a tube connected to the suction unit. The warm water irrigation unit provides warm water to the ear canal through the warm water line. The suction unit is in communication with the suspension suction tube and is configured to suction the suspension from the ear canal to a debris container.

BRIEF DESCRIPTION OF DRAWINGS

The foregoing summary, as well as the following detailed description of the invention, is better understood when read in conjunction with the appended drawings. For illustrating the invention, exemplary constructions of the invention are shown in the drawings. However, the invention is not limited to the specific components disclosed herein. The description of a component referenced by a numeral in a drawing is applicable to the description of that component shown by that same numeral in any subsequent drawing herein.

FIG. 1H illustrates an exploded view showing the motorized auger, a drill bit attached to the motorized auger, a warm water line, a suspension suction tube, an elbow connector, the threaded connector assembly, a union nut and the ear speculum.

FIG. 1I illustrates an assembled view of the components shown in FIG. 1H.

DETAILED DESCRIPTION OF THE INVENTION

Figure 1A:
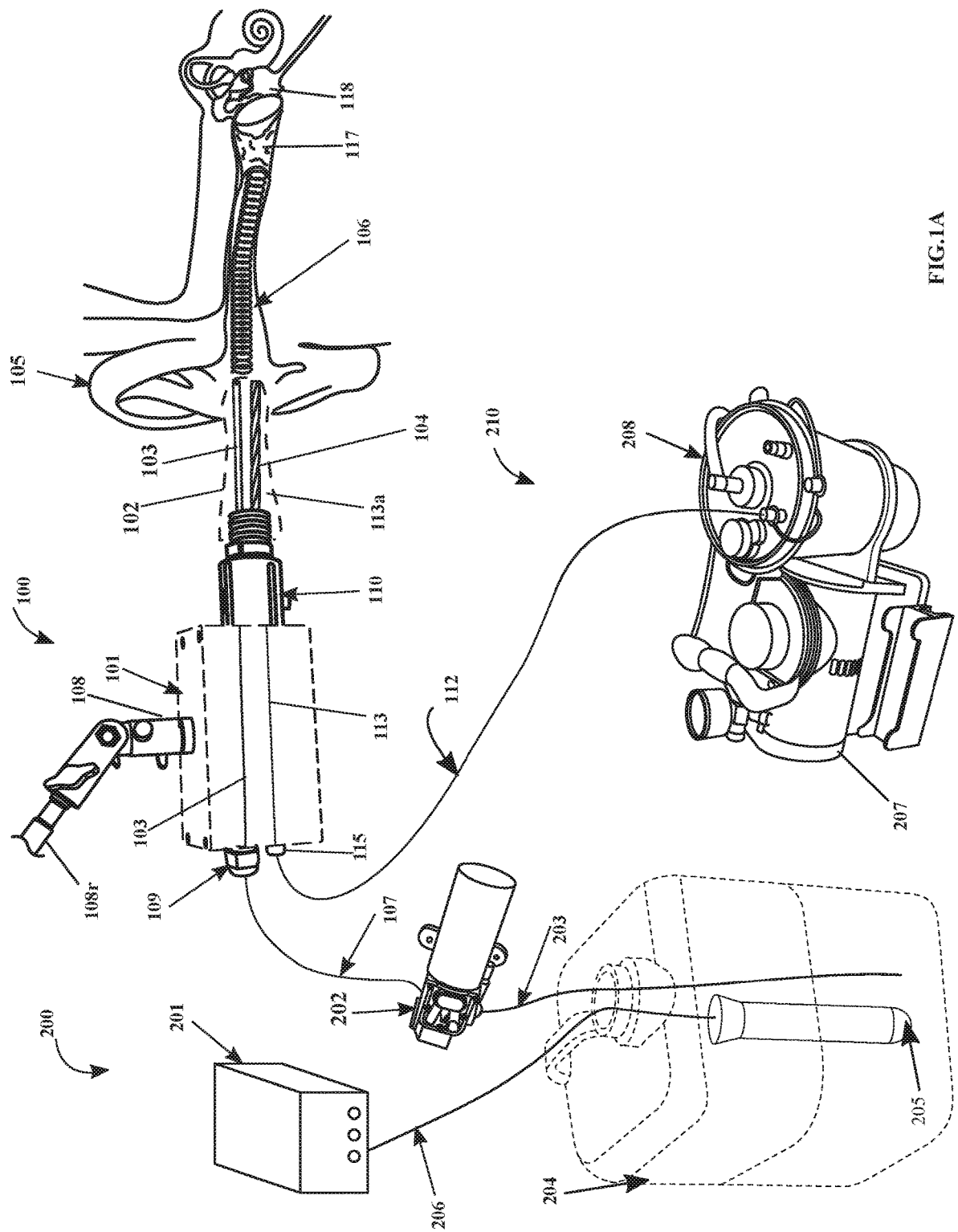
FIG. 1A exemplarily illustrates a schematic process flow of an ear disimpactor for disimpacting material impacted in an ear canal and material impacted against a tympanic membrane.

The foregoing summary, as well as the following detailed description of the invention, is better understood when read in conjunction with the appended drawings. For illustrating the invention, exemplary constructions of the invention are shown in the drawings. However, the invention is not limited to the specific components disclosed herein. The description of the component referenced by a numeral in a drawing is applicable to the description of that component shown by that same numeral in any subsequent drawing herein.

Figure 1B:
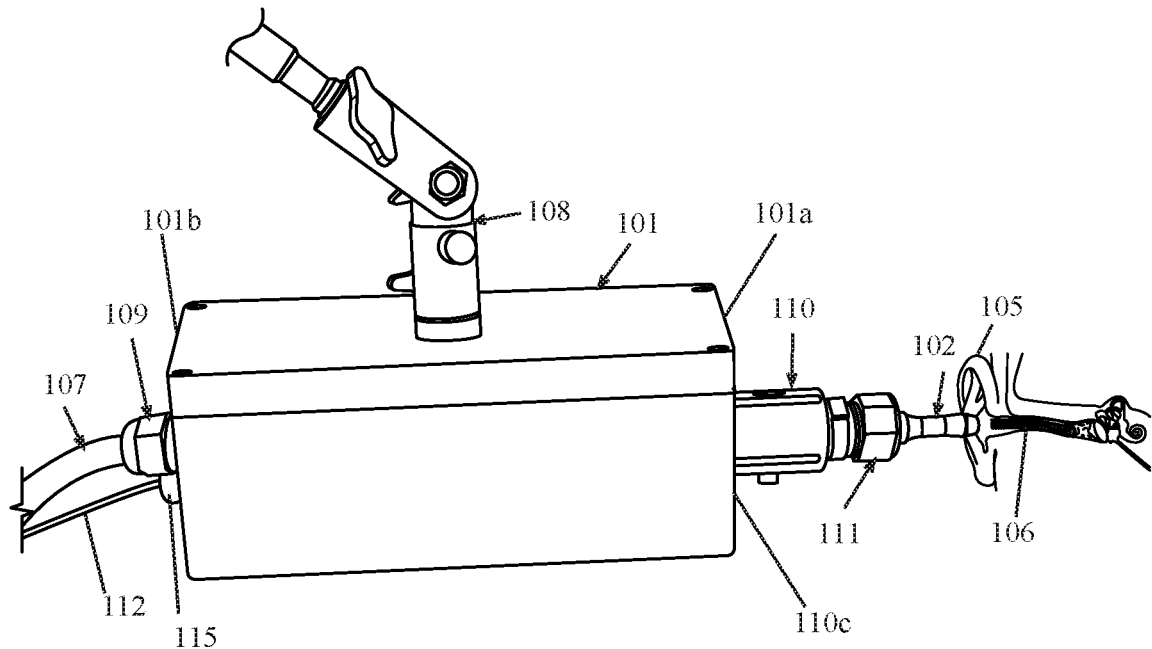
FIG. 1B exemplarily illustrates a front perspective view of a housing of the ear disimpactor showing an ear speculum attached to the housing, where the ear speculum is positioned on an outer ear.
Figure 1C:
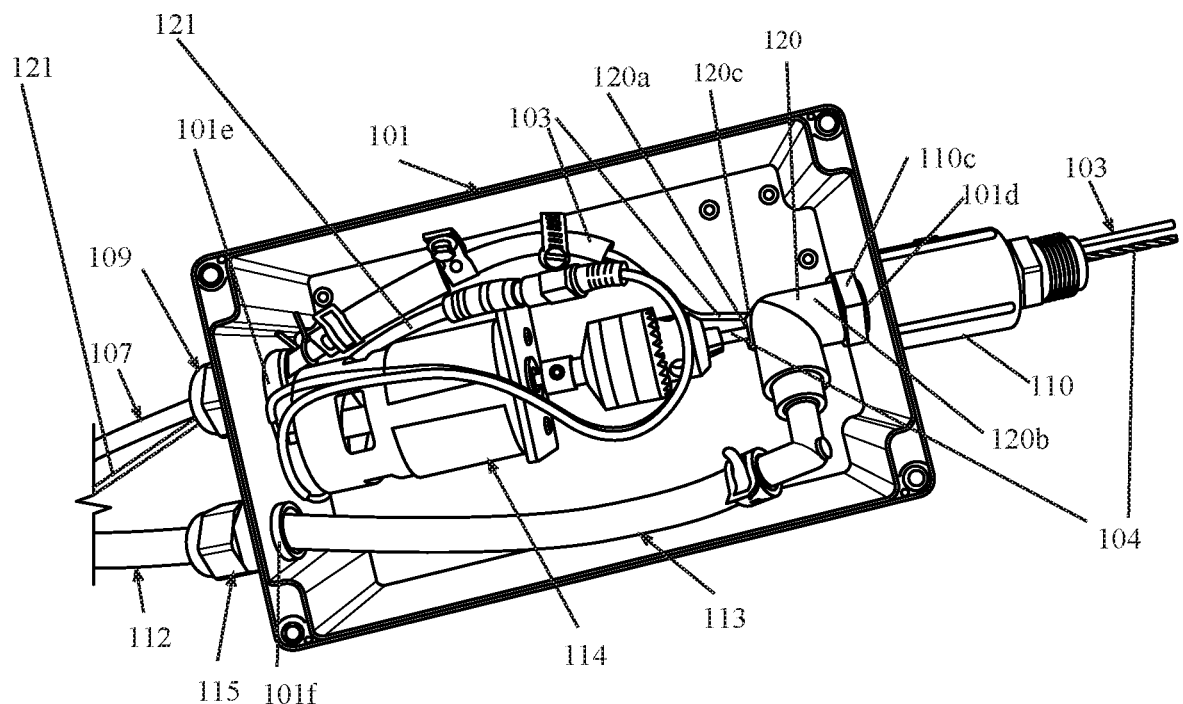
FIG. 1C exemplarily illustrates a top perspective view of the housing showing a motorized auger located inside the housing.

FIG. 1A exemplary illustrates a schematic process flow of an ear disimpactor 100 for disimpacting material 117 impacted in an ear canal 106 and material 117 impacted against the tympanic membrane 118, hereafter referred to as impacted material 117. The disimpactor 100 comprises a warm water irrigation unit 200, a container 204, a pump 202, a housing 101 comprising the motorized auger 114 shown in FIG. 1C, a warm water inlet line 107 in communication with the warm water line 103, as shown in FIG. 1C, a threaded connector assembly 110, an ear speculum 102 configured to engage with the outer ear 105, and a suction unit 210. The warm water irrigation unit 200 comprises the container 204 for storing water, a heating element 205 immersed in the water in the container 204, a temperature controller 201 for controlling the water temperature via a thermocouple 206 connected to the heating element 205, and the water pump 202 for suctioning warm water from the container 204 through tubing 203 and for pumping the warm water through the warm water inlet line 107 and the warm water line 103 that is in communication with the warm water inlet line 107, at a pre-set pressure between about 2 psig to about 20 psig through the ear speculum 102 to the ear canal 106, as illustrated in FIGS. 1A and 1E.

The suction unit 210 comprises a suction pump 207, a debris container 208, a suspension suction tube 113 shown in FIG. 1C, and a suction tube 112. The suction unit 210 is in communication with the suspension suction tube 113 which is in communication with the suction tube 112 as illustrated in FIGS. 1A and 1C. The drill bit 104 rotates concurrently at an entrance 119 of the ear canal 106 with the discharge of warm water from an end 103a of the water tube 103 in the ear canal 102 shown in FIG. 1E, and with the suction unit 210 in operation to disimpact the impacted material in the ear canal 102 and to suction the suspension out of the ear canal 106 and into the debris container 208. The tip 102a of the ear speculum 102 is in communication with the ear canal 106 at the entrance 119 of the ear canal 106. The inner portion 113a of the ear speculum 102 is in communication with the suspension suction tube 113 as illustrated in FIG. 1I. The suspension in the ear canal 106 proximal to the tip 102a of the ear speculum 102, and the suspension that drains to the inner portion 113a of the ear speculum 102 is continuously suctioned out of the ear canal 106 via the inner portion 113a of the ear speculum 102 when the drill bit 104 is rotating and the warm water is being fed to the ear canal 106 through the suspension suction tube 113 by the suction unit 210 via the suction tube 112. The suspension suctioned out of the ear canal 106 by the suction unit 210 is discarded in the debris container 208.

The drill bit 104 of the motorized auger 114 extends from the motorized auger 114 to the ear speculum 102, as shown in FIGS. 1H and 1I. The warm water inlet line 107 extends across the length of the housing 101, exits the housing 101 through the threaded connector assembly 110 and further extends towards the tip 102a of the ear speculum 102, as shown in FIG. 1A. The suction tube 112 extends as suspension suction tube 113 from a screwed fitting 115 to connect with an elbow connector 120, and through the threaded connector assembly 110 to the speculum 102. The ear speculum 102 is attached to the housing 101 on a first lateral surface 101a as shown in FIG. 1B. The ear speculum 102 is positioned by a boom 108 shown in FIG. 1G on an outer ear 105. The water in the container 204 is heated by the heating element 205 to a temperature set by the temperature controller 201 in the warm water irrigation unit 200. The warm water irrigation unit 200 is then actuated to irrigate the ear canal 106 by providing warm water from the container 204 of the warm water irrigation unit 200 to the ear canal 106 through the warm water inlet line 107 and the attached warm water line 103 shown in FIGS. 1A and 1E. When the warm water irrigation of the ear canal 106 is in progress, the suction pump 207 in the suction unit 210 and the motorized auger 114 are turned on. The warm water jetting into the ear canal 106 through warm water line 103, the suction in the ear canal 106 by the suction pump 207 provided via the suction tube 112 and the suspension suction tube 113, the inner portion 113a of the ear speculum 102, and the rotating drill bit 104 of the auger 114, creates a cyclonic action 116 inside the ear canal 106 as shown in FIG. 1E, resulting in the disimpaction of the impacted material 117 in the ear canal 106. The disimpacted impacted material 117 is moved to the entrance 119 of the ear canal 106 by the cyclonic action. At the entrance 119 of the ear canal 106, the rotating drill bit 104 grinds the impacted material into a suspension, while the warm water irrigation and suction is in progress. The suspension is suctioned by the suction unit 210 through the suspension suction tube 113 and the suction tube 112 to the debris container 208 shown in FIGS. 2A and 2B.

FIG. 1B exemplarily illustrates a front perspective view of the housing 101 of the ear disimpactor 100. The housing 101 is a rectangular box having the first lateral surface 101a at a distal end of the housing 101 and a second lateral surface 101 *b* at a proximal end of the housing 101. The ear speculum 102 is in communication with the housing 101 at a first lateral surface 101 *a* by the threaded connector assembly 110 connected to a first opening 101 *d*. A union nut 111 is slid around the ear speculum 102. The union nut 111 is then fastened to a first threaded end 110 *a* of the connector assembly 110 to secure the ear speculum 102 to the first threaded end 110 *a*. The ear speculum 102 is configured to engage an outer ear 105 as shown in FIG. 1E. A second threaded end 110 *b* illustrated in FIG. 1D of the connector assembly 110 is inserted into the housing 101 via the first opening 101 *d* and fastened to the housing 101 using nut 110 *c*. The drill bit 104 and the warm water line 103 are disposed within the ear speculum 102 when the housing 101 with the ear speculum 102 is positioned in the outer ear 105 as shown in FIG. 1B.

FIG. 1C exemplarily illustrates a top perspective view of the housing 101. The housing 101 comprises a motorized auger 114 comprising a drill bit 104, and a warm water line 103 entering the housing 101 through an opening 101*e* through a screwed fitting 109, and exiting the housing 101 through the screwed fittings 110*c* via the elbow connector 120. The housing 101 comprises a first opening 101*d* on the first lateral side 101*a*. The drill bit 104 and the warm water line 103 exit the housing 101 through the opening 101*d* via the elbow connector 120. The warm water line 103 extends across the length of the housing 101, through connector assembly 110 to a tip 102*a* of the ear speculum 102, as shown in FIGS. 1E and 1I. The housing 101 further comprises a suspension suction tube 113 that is an extension of the suction tube 112. A screwed fitting 115, as shown in FIG. 1C, is attached to an opening 101*f* of the housing 101. The screwed fitting 115 connects the suspension suction tube 113 to the suction tube 112 as the suspension suction tube 113 exits the housing 101 via the opening 101*f*. The suspension suction tube 113 extends from the screwed fitting 115 to connect with the elbow connector 120, and through the threaded connector assembly 110 to the speculum 102. The suspension suction tube 113 is in fluid communication with the inner portion 113*a* of the ear speculum 102, as illustrated in FIG. 1I. FIG. 1C also illustrates an electrical wiring 121 for powering the motorized auger 114. The electrical wiring 121 enters the housing 101 through the opening 101*e*. The electrical wiring 121 is connected to a main control unit 300 of the ear disimpactor 100. In an embodiment, the housing 101 comprises an elbow connector 120, as shown in FIG. 1C. The elbow connector 120 is, for example a 90° connector, as shown in FIGS. 1C, 1F, 1H and 1G. The elbow connector 120 connects to the first threaded end 110*a* of the connector assembly 110 as illustrated in FIGS. 1C, 1H and 1I. The elbow connector 120 comprises an opening 120*a* and another opening 120*b* on a bend of the elbow connector 120 for allowing the drill bit 104 and the warm water line 103 to extend through the elbow connector 120 and out of the housing 101 as shown in FIG. 1C. The opening 120*a* is oriented along an axis of the portion 120*b* of the elbow joint 120 that connects to the first threaded end 110*a* of the connector assembly 110. In an embodiment, the drill bit 104 and the warm water line 103 form an airtight seal with the openings 120*a* and 120*b*.

Figure 1D:
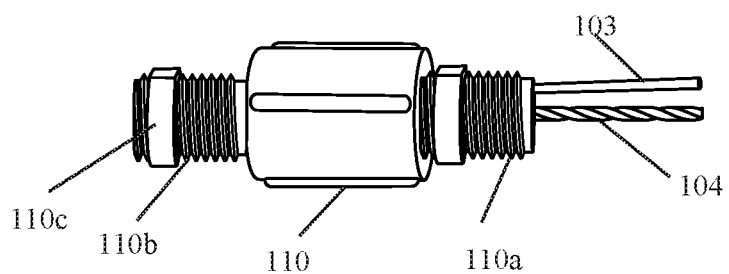
FIG. 1D exemplarily illustrates a threaded connector assembly for connecting the ear speculum to the housing of the ear disimpactor.
Figure 1E:
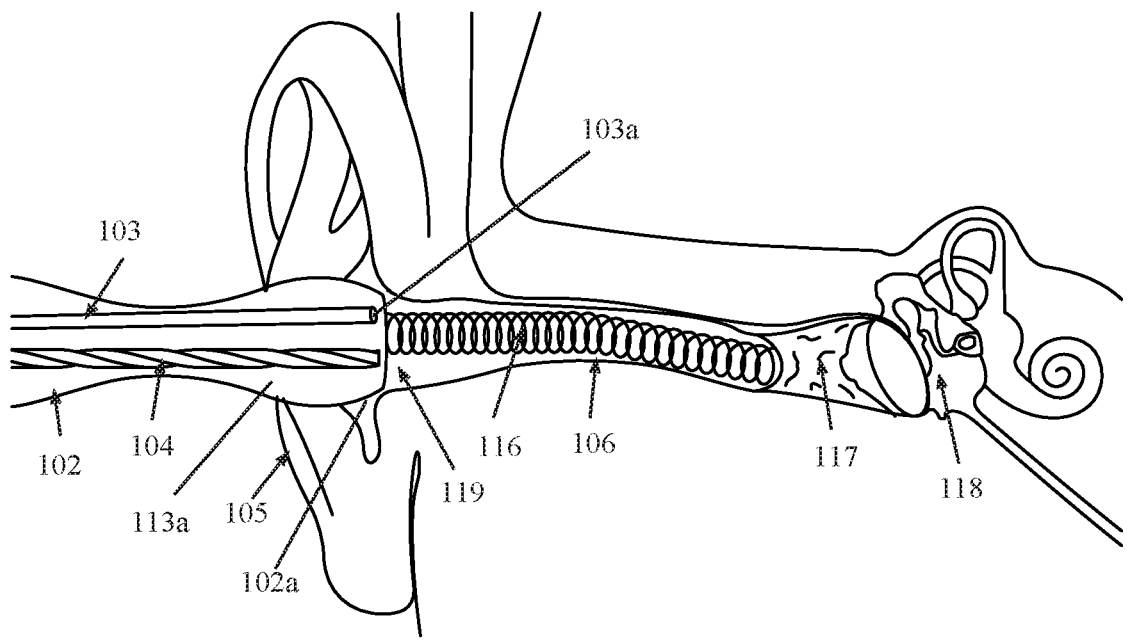
FIG. 1E exemplarily illustrates an enlarged view of the ear speculum positioned on the outer ear.

FIG. 1D exemplarily illustrates the threaded connector assembly 110 for connecting the ear speculum 102 to the housing 101 of the ear disimpactor 100. FIG. 1D also illustrates the drill bit 104 and the warm water line 103 disposed within the ear speculum 102. The drill bit 104 extends from the motorized auger 114 to the ear speculum 102, as illustrated in FIG. 1I.

Figure 1F:
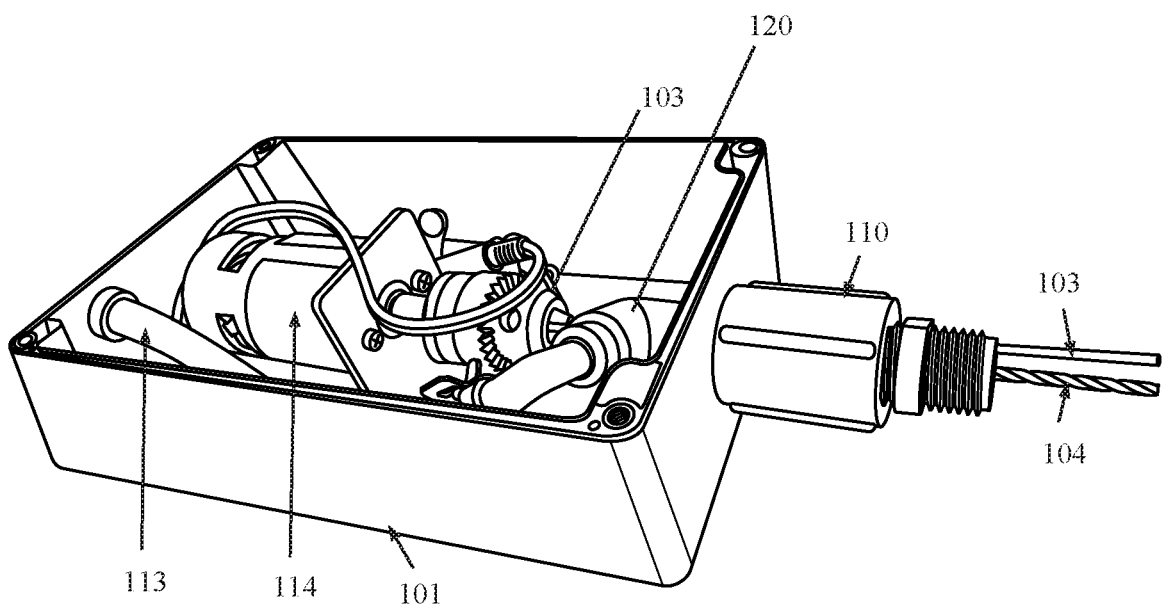
FIG. 1F exemplarily illustrates another top perspective view of the housing of the ear disimpactor showing internals of the housing.
Figure 1G:
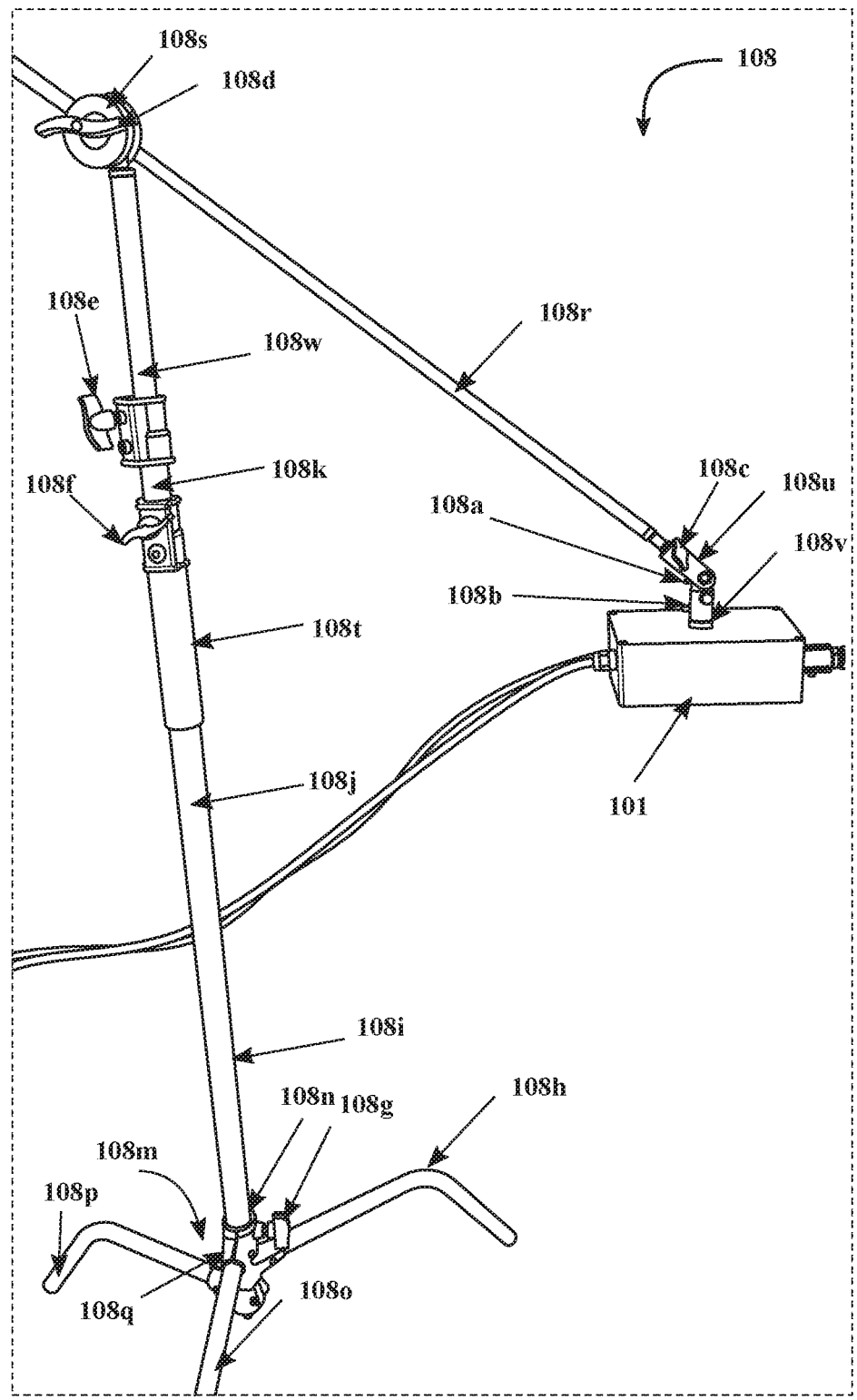
FIG. 1G exemplarily illustrates a side perspective view showing an arm of the boom attached to the housing of the ear disimpactor.

FIG. 1E exemplarily illustrates an enlarged view of the ear speculum 102 positioned on the outer ear 105. FIG. 1F exemplarily illustrates another top perspective view of the housing 101 of the ear disimpactor 100 showing internals of the housing 101. FIG. 1G exemplarily illustrates a side perspective view showing an arm of the boom 108 attached to the housing 101 of the ear disimpactor 100. The boom 108 carries the housing 101 and the ear speculum 102 attached to the housing 101. The boom 108 aids in positioning the ear speculum 102 at the entrance 119 of the ear canal 106 in the outer ear 105. The boom 108 is attached to a top surface of the housing 101. The boom 108 comprises three legs 108*h*, 108*o*, and 108*p* attached to the base 108*n* of a 3-section telescopic pole 108*i* in a tripod configuration 108*m*. The top most leg 108*o* is secured to the 3-section telescopic pole 108*i* through a locking collar 108*q* which allows the topmost leg 108*o* to slide along a lower section 108*j* of the 3-section telescopic pole 108*i* when a knob 108*g* of the locking collar 108*q* is loosened. The knob 108*g* of the locking collar 108*q* allows the topmost leg 108*o* to be fastened to any portion of the lower section 108*j* of the 3-section telescopic pole 108*i*, thereby enabling the boom 108 to be placed on uneven surfaces. The 3-section telescopic pole 108*i* further comprises a mid-section 108*k* which telescopically slides into the lower section 108*j*, and an upper section 108*w* which telescopically slides into the mid-section 108*k*. A locking collar 108*f* located at the top of the lower section 108*j* fastens the mid-section 108*k* to the lower section 108*j*. A knob in the locking collar 108*f* is loosened to extend or retract the mid-section 108*k*. A locking collar 108*e* located at the top of the mid-section 108*k* fastens the upper section 108*w* to the mid-section 108*k*. A knob in the locking collar 108*e* is loosened to extend or retract the upper section 108*w*. The boom 108 further comprises an arm 108*r* attached to an upper portion of the upper section 108*w* via a lockable swiveling grip head 108*s*. The lockable swiveling grip head 108*s* comprises a knob 108*d*. The knob 108*d* is loosened to slide the arm 108*r* in and out of the lockable swiveling grip head 108*s*, and to rotate the arm 108*r* along a vertical plane of the arm 108*r*. The lower section 108*j* of the 3-section telescopic pole 108*i* comprises a grip 108*t* attached proximal to the locking collar 108*f* of the lower section 108*j*. The boom 108 further comprises a locking swivel joint 108*u* attached to one end of the arm 108*r*. The locking swivel joint 108*u* comprises a socket into which the end of the arm 108*r* is inserted. A knob 108*c* is used to fasten the locking swivel joint 108*u* to the end of the arm 108*r*. The housing 101 is attached to a shank 108*v* of the locking swivel joint 108*u*. A knob 108*b* is used to fasten or remove the housing 101 to and from the shank 108*v*. A knob 108*a* in the locking swivel joint 108*u* fastens or loosens the swivel joint in the locking swivel joint 108*u*, enabling the housing 101 to be rotated along a vertical plane and a horizontal plane. The knob 108*a* is fastened to lock the housing 101 and the ear speculum 102 in a desired position on the outer ear 105. Loosening one of the knobs of the locking collars 108*e* and 108*f* allows the arm 108*r* to be rotated in a horizontal plane.

FIG. 1H illustrates an exploded view showing the motorized auger 114, the drill bit 104 attached to the motorized auger 114, the warm water line 103, the suspension suction tube 113, the elbow connector 120, the threaded connector assembly 110, the union nut 111 and the ear speculum 102. FIG. 1I illustrates an assembled view of the components shown in FIG. 1H. As explained above, the drill bit 104 and the warm water line 103 form an airtight seal with the openings 120*a* and 120*b* in the elbow connector 120. The suspension suction tube 113 also forms an airtight seal with the elbow connector 120. Due to the airtight seals, the suspension is sucked only through the tip 102a of the ear speculum 102 when the suction pump 207 is activated, as shown by arrow near the tip 102a of the ear speculum 102. The suspension suctioned by the suction unit 210 passes through the ear speculum 102, the connector assembly 110, the elbow connector 120, and into the suspension suction tube 113, as shown by arrows in FIG. 1I.

Figure 1J:
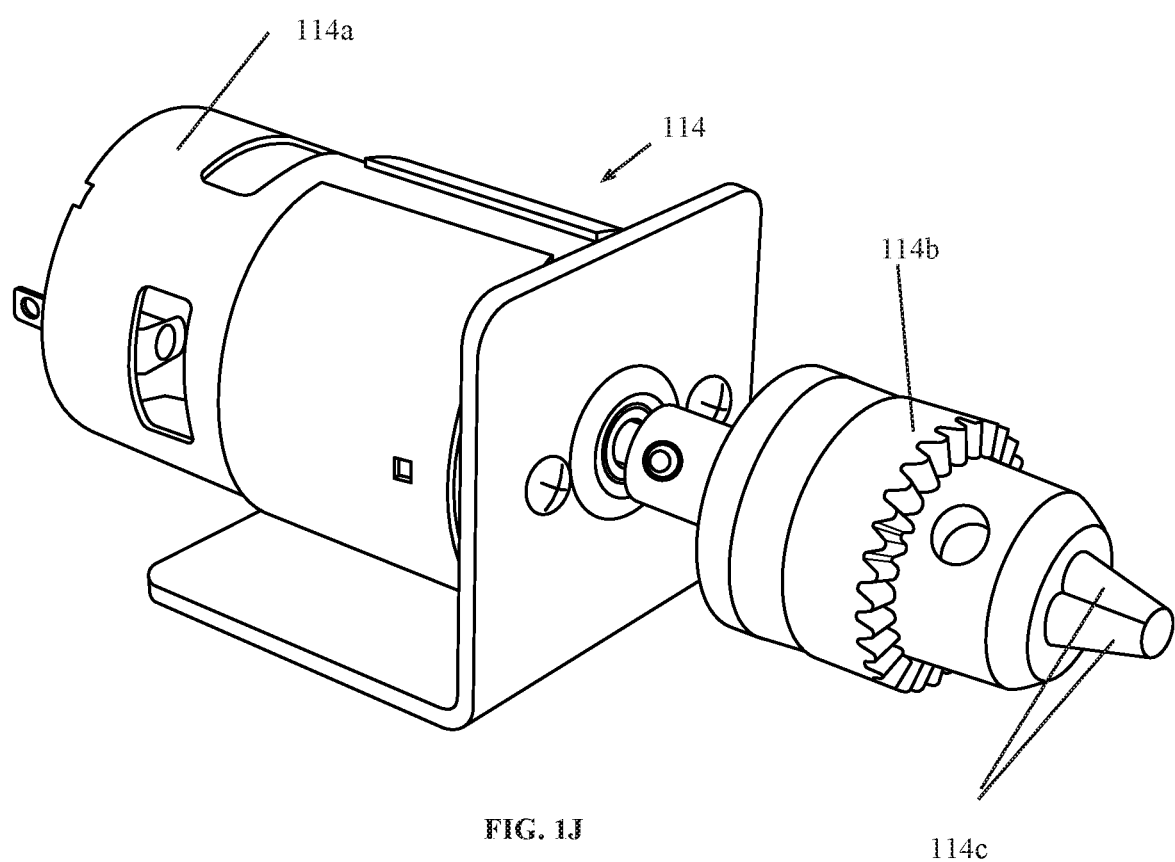
FIG. 1J exemplarily illustrates a motor used for the auger shown in FIG. 1C.

FIG. 1J exemplarily illustrates a motor 114a used for the motorized auger 114 shown in FIG. 1C. The motorized auger 114 comprises a drill chuck 114b comprising jaws 114c that are configured to secure a drill bit 104 to the motorized auger 114. The drill bit 104, illustrated in FIGS. 1A, 1C-1F, 1H and 1I rotates when the motorized auger 114 is actuated. The motor is, for example, a 12V DC motor. In an embodiment, the drill bit 104 is made of plastic, wood, or any other material that is softer compared to metal. In an embodiment, the drill bit 104 is made of metal.

Figure 2A:
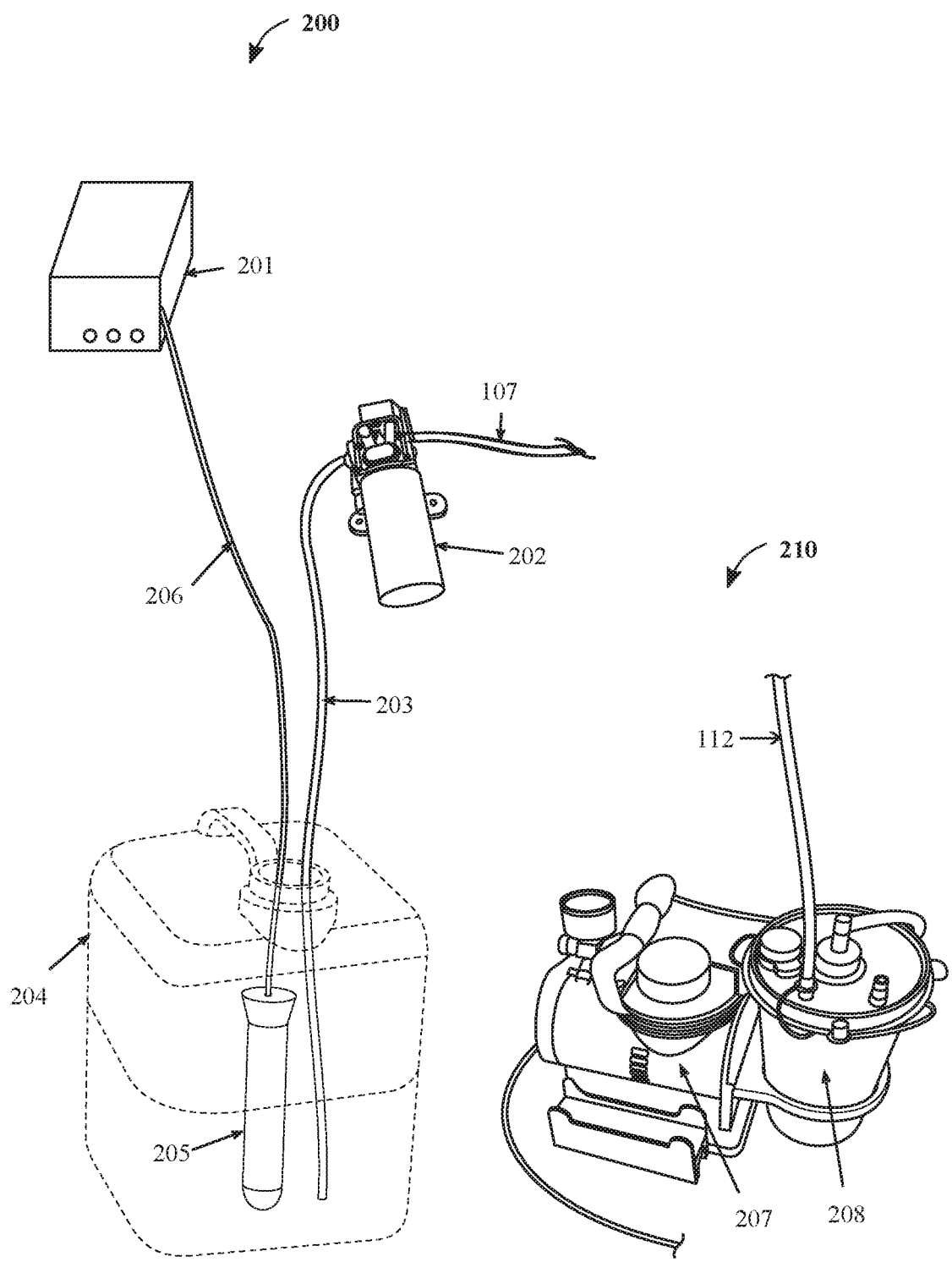
FIG. 2A exemplarily illustrates a larger view of the warm water irrigation unit and the suction unit.

FIG. 2A exemplarily illustrates a larger view of the warm water irrigation unit 200 and the suction unit 210. The suction unit comprises a suction pump 207, a debris container 208, and a suction tube 112. The suction pump 207 extracts the suspension comprising the cerumen, the insects, and other debris 117 and water, from the ear canal 106 by creating suction to suck the suspension from the ear canal 106 through the suspension suction tube 113, and the suction tube 112 and thereafter to discard the suspension in the debris container 208. In an embodiment, the inner portion 113a, illustrated in FIG. 1E, of the ear speculum 102 acts as an extension of the suspension suction tube 113. In an embodiment, the suction unit 210 is operated substantially simultaneously with the irrigation of the ear canal 106 by warm water unit 200 and rotation of the drill bit 104 of the auger 114.

Figure 2B:
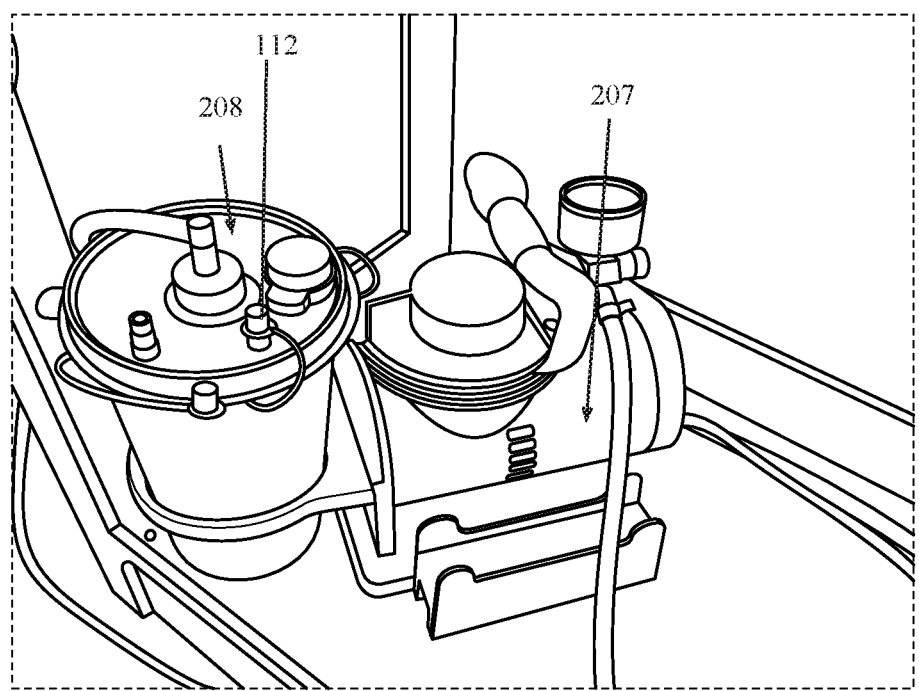
FIG. 2B exemplarily illustrates a close-up view of a suction pump and a debris container of the suction unit shown in FIG. 2A.
Figure 2C:
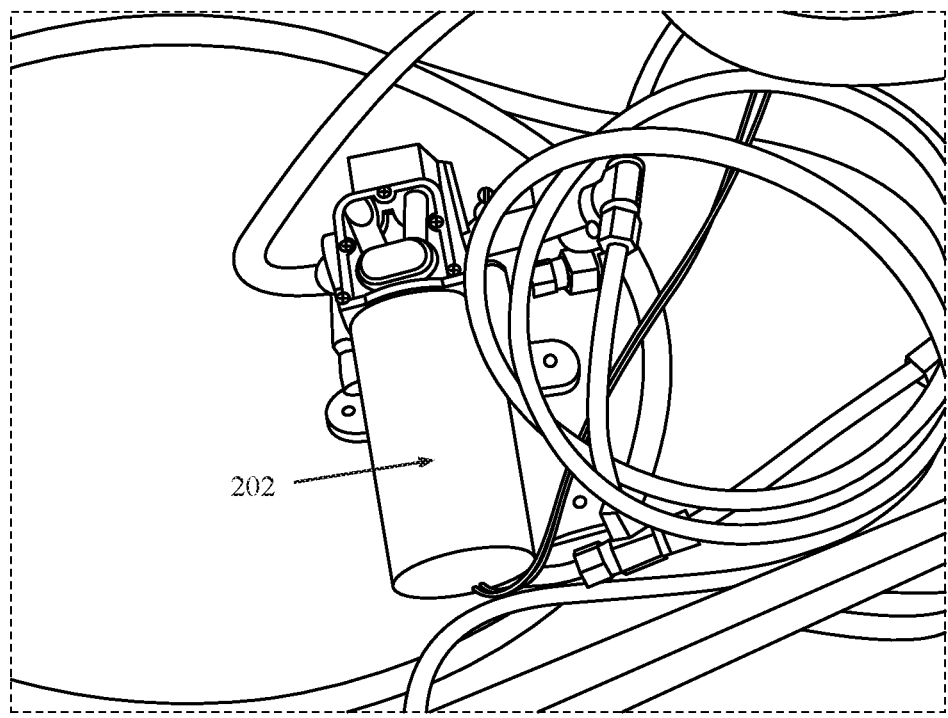
FIG. 2C exemplarily illustrates a close-up view of a water pump of the warm water irrigation unit shown in FIG. 2A.
Figure 2D:
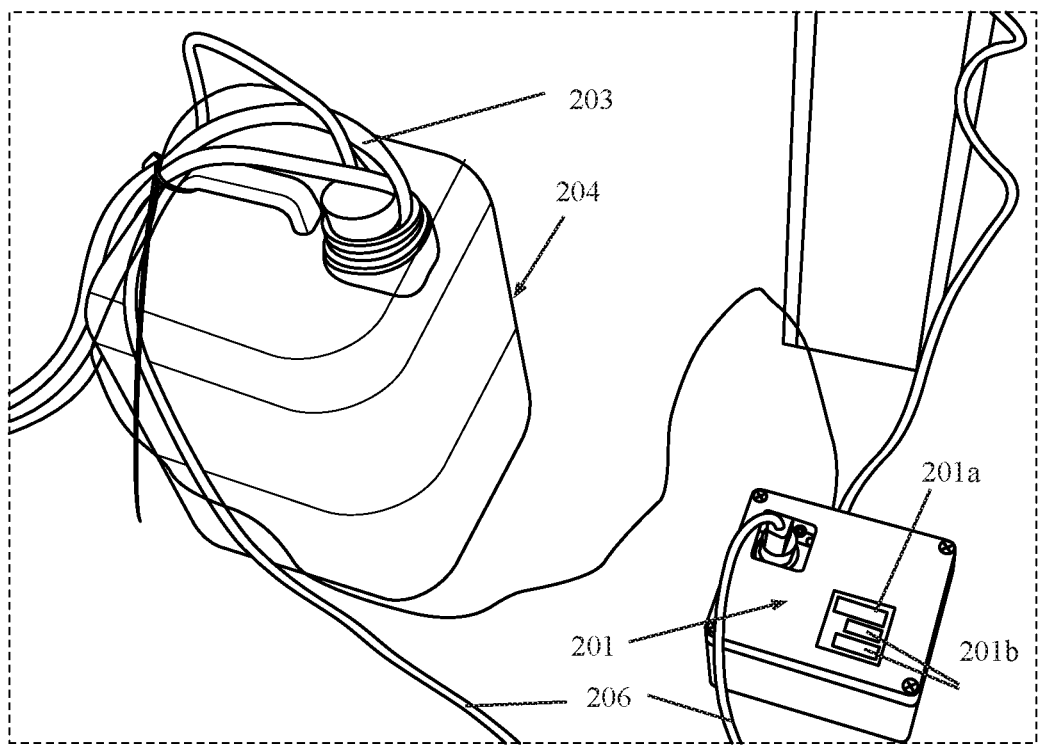
FIG. 2D exemplarily illustrates a top perspective view showing a warm water container and a temperature controller of the warm water irrigation unit shown in FIG. 2A.

FIG. 2B exemplarily illustrates a close-up view of the suction pump 207 and a debris container 208 of the suction unit 210 shown in FIG. 2A. FIG. 2C exemplarily illustrates a close-up view of the water pump 202 of the warm water irrigation unit 200 shown in FIG. 2A. FIG. 2D exemplarily illustrates a top perspective view showing the container 204 and a temperature controller 201 of the warm water irrigation unit 200 shown in FIG. 2A. In an embodiment, the temperature controller 201 comprises a display 201a for displaying a temperature that is set for a heating element 205 in the container 204. In another embodiment, the temperature controller 201 further comprises switches 201b to increase or decrease the temperature of the heating element 205 in the container 204.

Figure 3:
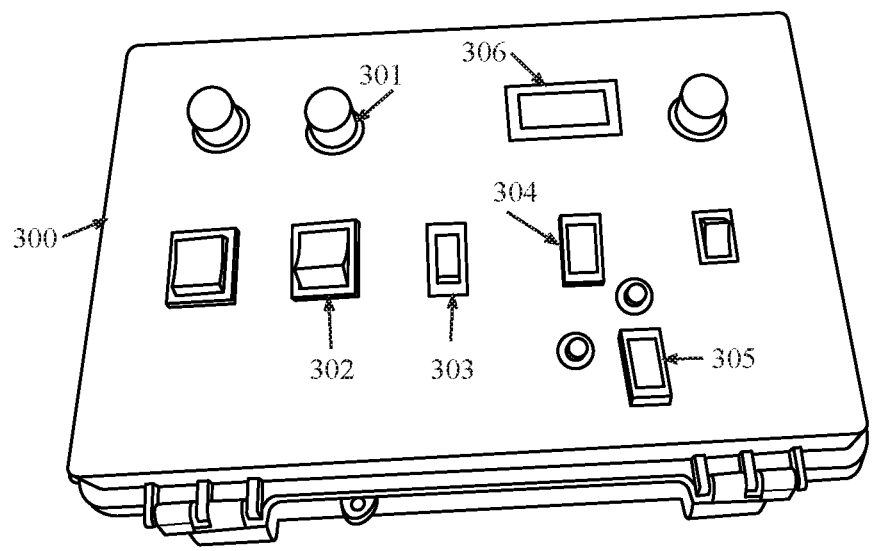
FIG. 3 exemplarily illustrates a main control unit of the ear disimpactor.

FIG. 3 exemplarily illustrates a main control unit of the ear disimpactor 100. The main control unit 300 comprises a set of switches 301-305, and a display 306. The switches 301-305 comprise a first switch 305 for switching on or switching off the main control unit 300, a second switch 302 for switching on or switching off the 12V DC motor of the motorized auger 114, a speed control dial 301 for controlling speed of rotation of the drill bit 104 of the motorized auger 114, a third switch 303 for switching on or switching off the water pump 202 of the warm water irrigation unit 200, and a fourth switch 304 for switching on or switching off the suction pump 207 of the suction unit 210. In an embodiment, the display 306 displays temperature of warm water as measured by the temperature controller 201.

To disimpact the impacted material impacted within an ear canal 106 and against a tympanic membrane 118, where the impacted material comprises the cerumen, the insects, and the other debris 117, the warm water irrigation unit 200, the motorized augur 114, and the suction pump 202 are activated simultaneously. The warm water irrigation unit 200 jets the warm water into the ear canal 106 through the warm water inlet line 107 and the warm water line 103. The motorized auger 114 simultaneously rotates the drill bit 104 at the entrance of the ear canal 106. The suction pump 202 simultaneously starts suction through the suspension suction tube 113. The jetted warm water, the rotating drill bit 104, and the suction together create a cyclonic action 116 within the ear canal 106, as shown in FIG. 1E. The cyclonic action 116 and the suction moves the impacted material 117 from the ear canal 106 and near the tympanic membrane 118 to an entrance 119 of the ear canal 106. At the entrance 119 of the ear canal 106, the rotating drill bit 104 grinds the impacted material 117 into a suspension and the suction unit 210 extracts the suspension from the entrance 119 of the ear canal 106 by suction via the suspension suction tube 113 and the suction tube 112.

Figure 4:
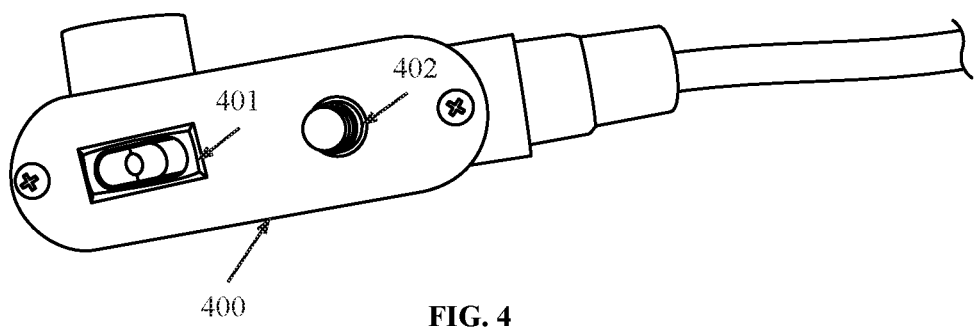
FIG. 4 exemplarily illustrates a hand-held control unit for a patient to control the ear disimpactor.

FIG. 4 exemplarily illustrates a hand-held control unit 400 for a patient to control an ear disimpactor 100. After switching on the suction pump 207 and the motorized auger 114 using the switches 304 and 302 respectively, on a main control unit 300, and after adjusting a rotation speed of a drill bit 104 of a motorized auger 114 using a speed control dial 301 on the main control unit 300, the patient uses the hand held unit 400 to switch on or off the main controller unit 300 and a water pump 202 to provide warm water irrigation into an ear canal 106. The suction applied by a suction pump 207, the rotation of the motorized auger 114, and warm water jetting into the ear canal 106 together create a cyclonic action 116 inside the ear canal 106, to move impacted material comprising cerumen, insects, and other debris 117 from a tympanic membrane 118 to an entrance 119 of the ear canal 106. At the entrance 119 of the ear canal 106, the rotating drill bit 104 of the motorized auger 114 grinds the impacted material 117 into a suspension. The suspension is simultaneously suctioned into the debris container 208.

The ear disimpactor 100 is configured to be manufactured in both hand-held and miniature versions depending upon whether the ear disimpactor 100 is used for removing the impacted material 117 from adults, children or babies. The cyclonic action moves the impacted material 117 from the ear canal and near the tympanic membrane 118 to the entrance 119 of the ear canal 106, for subsequent grinding of the impacted material 117 into the suspension, followed by suctioning of the suspension out of the ear canal 106, thereby facilitating painless and effective removal of the impacted material 117 out of the ear canal 106.

The foregoing examples have been provided merely for explanation and are in no way to be construed as limiting of the ear disimpactor 100 disclosed herein. While the ear disimpactor 100 has been described with reference to a particular embodiment, it is understood that the words, which have been used herein, are words of description and illustration, rather than words of limitation. Furthermore, although the ear disimpactor 100 has been described herein with reference to a particular means, materials, and embodiment, the ear disimpactor 100 is not intended to be limited to the particulars disclosed herein; rather, the design and functionality of the ear disimpactor 100 extends to all functionally equivalent structures and uses, such as are within the scope of the appended claims. Furthermore, it will be understood by those skilled in the art, having the benefit of the teachings of this specification, that the ear disimpactor 100 disclosed herein is capable of modifications and other embodiments may be effected and changes may be made thereto, without departing from the scope and spirit of the ear disimpactor 100 disclosed herein.

I claim:

1. An ear disimpactor for disimpacting material impacted in an ear canal and against a tympanic membrane, wherein said impacted material comprises cerumen, insects, and other debris, and wherein said ear disimpactor comprises:
   a housing, said housing comprising:
      an ear speculum attached to an outer surface of said housing;
      a motorized auger comprising a drill bit;
      said drill bit extending from said motorized auger to a tip of said ear speculum;
      a warm water line extending from said tip of said ear speculum and across a length of said housing;
      a suspension suction tube extending from said tip of said speculum and across said length of said housing, wherein said warm water line and said suspension suction tube further extend out of said housing through one or more openings located at a proximal end of said housing;
   a warm water irrigation unit for providing warm water to said ear canal through said warm water line, wherein said warm water irrigation unit irrigates said ear canal with the warm water through said warm water line, and wherein said warm water irrigation unit comprises:
      a water pump for pumping said warm water;
      a container for storing said warm water;
      a heater for heating water inside said container to a required temperature;
      a temperature controller; and
      a warm water inlet line for supplying said warm water from said water pump to said warm water line in said housing;
   said warm water irrigation unit, said motorized augur, and a suction pump of a suction unit configured to be activated substantially simultaneously, wherein said warm water irrigation unit is configured to jet said warm water into said ear canal through said warm water inlet line and said warm water line, wherein said motorized auger is configured to simultaneously rotate said drill bit, wherein said suction pump is configured to simultaneously begin suction through said suspension suction tube and a suction tube, wherein said jetted warm water, said suction, and said rotating drill bit are configured to create a cyclonic action within said ear canal to move said impacted material from said tympanic membrane to an entrance of said ear canal, wherein said rotating drill bit of said motorized auger is configured to grind said impacted material, and wherein said suspension suction tube is configured to extract a suspension comprising said grinded impacted material and said warm water from said entrance of said ear canal;
   and said suction unit in communication with said suspension suction tube for suctioning out said suspension comprising said grinded impacted material and the warm water.

2. The ear disimpactor of claim 1, further comprising a boom for carrying said housing, wherein said boom is attached to a top surface of said housing, and wherein said boom is configured to position said ear speculum on an outer ear.

3. The ear disimpactor of claim 1, wherein said motorized auger comprises a motor for rotating said drill bit, and wherein said motor is a 12V DC Motor.

4. The ear disimpactor of claim 1, wherein said suction unit comprises:
   said suction pump for extracting said suspension from said ear canal by creating suction;
   a debris container for storing said suspension extracted by said suction pump; and
   said suction tube for discharging said suspension comprising said grinded impacted material and said warm water from said suspension suction tube to said debris container.

5. The ear disimpactor of claim 1, further comprises a main control unit, comprising:
   a first switch for switching on or switching off the main control unit;
   a second switch for switching on or switching off a 12V DC motor of said motorized auger;
   a speed control dial for controlling rotating speed of said drill bit of said motorized auger;
   a third switch for switching on or switching off said water pump of said warm water irrigation unit; and
   a fourth switch for switching on or switching off said suction pump of said suction unit.

6. The ear disimpactor of claim 5, further comprises a hand-held control unit comprising:
   a fifth switch for switching on or switching off said main control unit; and
   a sixth switch for switching on or switching off said water pump of said warm water irrigation unit.

7. A method for disimpacting impacted material from an ear canal, comprising:
   providing an ear disimpactor comprising:
      a housing, said housing comprising:
         an ear speculum attached to an outer surface of said housing;
         a motorized auger comprising a drill bit;
         said drill bit extending from said motorized auger to a tip of said ear speculum;
         a warm water line extending from said tip of said ear speculum and across a length of said housing;
         a suspension suction tube extending from said tip of said speculum and across said length of said housing, wherein said warm water line and said suspension suction tube further extend out of said housing through one or more openings located at a proximal end of said housing;
      a warm water irrigation unit; and
      a suction unit in communication with said suspension suction tube;
   positioning said ear speculum on an outer ear;
   irrigating the ear canal of the ear by providing warm water by said warm water irrigation unit through said warm water line, wherein irrigating the ear canal of the ear comprises:
      activating substantially simultaneously said warm water irrigation unit, said motorized augur, and a suction pump of said suction unit, wherein said warm water irrigation unit is configured to jet said warm water into said ear canal through said warm water line, wherein said motorized auger is configured to simultaneously rotate said drill bit, and wherein said suction pump is configured to simultaneously begin suction through said suspension suction tube and a suction tube; and
   creating a cyclonic action within said ear canal by said jetted warm water, said suction, and said rotating drill bit;

moving said impacted material comprising cerumen, insects, and other debris from a tympanic membrane to an entrance of said ear canal using said cyclonic action;
grinding said impacted material by said rotating drill bit of said motorized auger; and
extracting a suspension comprising grinded impacted material and said warm water from said entrance of said ear canal through said suspension suction tube.

8. The method of claim 7, further comprising controlling a rotation speed of said drill bit using a speed control dial on a main control unit of said ear disimpactor.

9. A method for disimpacting impacted material from an ear canal, comprising:
provinding an ear disimpactor, comprising:
a housing, comprising:
a motorized auger comprising:
a motor; and
a drill bit;
a warm water line; and
a suspension suction tube;
an ear speculum attached to said housing, wherein said warm water line and said drill bit extend out of a distal end of said housing up to a tip of said ear speculum;
a warm water irrigation unit for jetting warm water into the ear canal via a warm water inlet line and said warm water line; and
a suction unit for suctioning suspension from said ear canal, wherein said suspension comprises grinded impacted material and said warm water;
moving said ear speculum attached to said housing into an outer ear using a boom attached to said housing;
activating said warm water irrigation unit, said motorized auger, and said suction unit substantially simultaneously to create a cyclonic action within said ear canal to move said impacted material from a tympanic membrane to an entrance of said ear canal;
grinding said impacted material at said entrance of said ear canal, by said drill bit of said motorized auger; and
suctioning out said suspension comprising said grinded impacted material and said warm water, by a suction pump of said suction unit.

10. An ear disimpactor for disimpacting impacted material from an ear canal, comprising:
a housing, comprising:
a motorized auger comprising:
a motor; and
a drill bit;
a warm water line; and
a suspension suction tube;
an ear speculum attached to said housing, wherein said warm water line and said drill bit extend out of a distal end of said housing up to a tip of said ear speculum;
a warm water irrigation unit for jetting warm water into an ear canal via a warm water inlet line and said warm water line; and
a suction unit for suctioning suspension from said ear canal into a debris container, wherein said suspension comprises grinded impacted material and said warm water, wherein after moving said ear speculum attached to said housing into an outer ear using a boom attached to said housing, said warm water irrigation unit, said motorized auger, and a suction pump of said suction unit are substantially simultaneously activated to create a cyclonic action within said ear canal to move said impacted material from a tympanic membrane to an entrance of said ear canal, and wherein rotation of said drill bit of said motorized auger grinds said impacted material at said entrance of said ear canal.

* * * * *